United States Patent [19]
Schubert

[11] 4,196,285
[45] Apr. 1, 1980

[54] ANTIBIOTIC PURIFICATION PROCESS

[75] Inventor: Paul F. Schubert, New York, N.Y.

[73] Assignee: Merck & Co., Inc., Rahway, N.J.

[21] Appl. No.: 919,649

[22] Filed: Jun. 28, 1978

Related U.S. Application Data

[63] Continuation of Ser. No. 802,710, Jun. 2, 1977, abandoned.

[51] Int. Cl.$^2$ .................................. C07D 501/02
[52] U.S. Cl. ........................................... 544/20
[58] Field of Search ................................ 544/20

[56] References Cited

U.S. PATENT DOCUMENTS

| | | | |
|---|---|---|---|
| 3,709,880 | 1/1973 | Goegelman et al. | 544/20 |
| 3,983,108 | 9/1976 | Bines | 544/20 |

*Primary Examiner*—Nicholas S. Rizzo
*Attorney, Agent, or Firm*—Hesna J. Pfeiffer; Julian S. Levitt

[57] ABSTRACT

Cephamycin C is concentrated and purified by subjecting a fermentation broth which contains Cephamycin C to the following sequence of steps: filtration at acidic pH, passage through a methylene sulfonic acid cation ion exchange resin, washing with an aqueous stream having a low concentration of Cephamycin C, and elution using the above aqueous stream from the previous step, recirculated and maintained at an elevated pH.

4 Claims, No Drawings

ANTIBIOTIC PURIFICATION PROCESS

RELATIONSHIP TO PRIOR APPLICATIONS

This application is a continuation of Ser. No. 802,710, filed June 2, 1977, now abandoned.

BACKGROUND OF THE INVENTION

The present invention relates to the concentration and purification of Cephamycin C. More particularly it relates to the concentration and purification of Cephamycin C from a fermentation broth which contains Cephamycin C.

Cephamycin C is a cephalosporin antibiotic having the structural formula

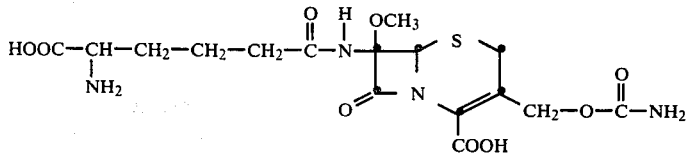

The preparation of this antibiotic by a fermentation process is reported by Stapley et al., Antimicrobial Agents and Chemotherapy, September 1972, pp. 122–131. In such a process it is necessary to separate the desired product from large volumes of liquid containing large amounts of undesired materials. Such separation is time consuming and expensive.

There are a number of previous processes to prepare purified Cephamycin C. U.S. Pat. No. 3,733,320 relates to a multi-step process involving at least two resin columns, one cationic, the second anionic. U.S. Pat. No. 3,983,108 involves adsorption of Cephamycin C on activated carbon followed by solvent elution. Both of these processes result in lower yields than in the instant process, due in part to product decomposition. A disadvantage of the carbon process is the large consumption of relatively expensive solvent while the sequential resin column purification process results in a dilute processing stream, requiring additional concentration time.

It is, accordingly, an object of the present invention to provide an improved method for obtaining Cephamycin C from a fermentation broth. Another object is to provide a method for concentrating and purifying Cephamycin C from a fermentation broth in which it has been prepared. A further object is to provide a simple and economical process for concentrating and purifying Cephamycin C from a fermentation broth. These and other objects of the present invention will be apparent from the following description.

SUMMARY OF THE INVENTION

Cephamycin C is concentrated and purified by subjecting a fermentation broth which contains Cephamycin C to the following sequence of steps: filtration at an acidic pH, passage through a methylene sulfonic acid cation ion exchange resin, washing with an aqueous stream containing a small amount of Cephamycin C, partial displacement using 10% NaCl solution, then elution using this recirculating stream, at an adjusted pH, from the previous two steps.

DETAILED DESCRIPTION

Cephamycin C is prepared according to the fermentation process described by Stapley et al. supra. At the end of the fermentation Cephamycin C is present in a large volume of liquid containing significant quantities of undesired organic and inorganic materials. According to the present invention, the Cephamycin C present in such a fermentation broth is concentrated and purified by a sequence of operations involving acidification, filtration, passage through an ion exchange column, washing with an aqueous spent broth containing a small amount of Cephamycin C, and then elution of the recirculating aqueous spent broth at an elevated pH. Each step will now be described in detail. One important condition maintained throughout all steps is the maintenance of the reactant temperatures of between about 05° C. to minimize decomposition losses.

A. The fermentation broth is acidified to a pH of from about 1.5 to about 4.5, preferably to a pH of about 1.8–2.5 by the addition of acid, preferably a mineral acid for reasons of economy, and most preferably, $H_2SO_4$. The acidified broth is then filtered, preferably after adding a filter aid such as, for example, diatomaceous earth.

B. The filtrate is passed downflow through a cation ion exchange resin, preferably a methylene sulfonic acid cation ion-exchange resin, having a particle size of between about 30–60, U.S. Standard sieve size. A suitable resin is Duolite C-3, trademark of Diamond Shamrock Corporation. The filtrate is passed at a rate of about 0.6 bed volumes to 2 bed volumes per hour, so that the pseudo contact time is between about 20 to 100 minutes (residence time of ) filtrate in the column).

C. The column is then washed with either water or an aqueous stream containing a small amount of Cephamycin C, obtained from a tail cut from a previous operation, generally contains between about 5–6% Cephamycin C of the original change. A sufficient volume of wash is used to displace the column volume once.

D. The column is then at least partially displaced by eluting with up to one bed volume of an aqueous sodium chloride solution, 5–15%, and preferably about 10%.

E. The streams from both Steps C and D are then combined and recirculated through the column. A sufficient amount of a suitable base, such as sodium hydroxide, is added to raise the pH to about 7 and 8. This stream is then circulated through the column to elute the Cephamycin C. The end point is reached when the pH of the exit stream is between 5 and 6.5, preferably 5.5. Generally, this involves a recirculation of 3–5 hours or 10–15 times.

The concentrated purified solution can then be used to prepare either the solid purified Cephamycin C, or further treated chemically to form antibiotically active derivatives.

The following examples illustrate the present invention.

EXAMPLE 1

A 23 gallon column 12 inches in diameter was filled with Duolite C-3 ion exchange resin having a particle size of between 40 and 60 U.S. Standard sieve mesh. A Cephamycin C fermentation broth was acidified to pH 3.5 by the addition of dilute (10%) sulfuric acid, approximately 5% acid solution by volume is required. A diatomaceous earth filter aid was added and the fermentation broth filtered. The activity titer of the filtrate and all combined filter-cake washes was 0.7 grams per liter. The pH was adjusted to 1.8 by dilute $H_2SO_4$. This material was fed at a rate of 2–3 bed volumes per hour until a total of 6.9 bed volumes had been loaded. The resin was then washed with 1 displacement volume (approximately 15 gal.) of cold water at the same flow rate. An eluting solution consisting of 2 kg. sodium chloride dissolved in 10 gallons cold water was fed onto the column. The Cephamycin C was eluted from the resin by recirculating this solution through the column; the pH of the recirculating solution was continually adjusted to pH 7.0–8.0 by the addition of dilute (5%) sodium hydroxide to the stream. (~3–4 gallons dilute sodium hydroxide were required.) The procedure was continued until the pH of the effluent was greater than 5.5. The column was then displaced with 50 gallons of chilled water, and divided into two portions, a rich cut and a tail cut. The rich cut contained 90% of the original amount of Cephamycin C and the tail cut 1%. The leakage of Cephamycin C through the resin was 5%. The temperature of reactants was maintained at 0–5° C. throughout.

EXAMPLE 2

The same feed procedure as in Example 1 except that a 200 gallon column was used. The activity titer of the feed was 1.01 grams per liter. 4.7 Bed volumes of feed were put on the column at a rate of 3.5 gallons per minute. A 400 gallon rich cut obtained following recirculation at the adjusted pH contained 94% Cephamycin C. The tail cut contained 4% Cephamycin C.

What is claimed is:

1. A process for separating Cephamycin C from fermentation broth impurities which comprises (a) passing a filtrate of a fermentation broth containing Cephamycin C at a pH of from about 1.8 to about 2.5 through a cation ion exchange resin having a particle size of 30–60 U.S. Standard size; (b) washing the column with 1–2 bed volumes of either water or a dilute aqueous stream containing a small amount of Cephamycin C; (c) displacing up to 1 bed volume with 10% aqueous sodium chloride; (d) eluting with the recirculating streams combined from the previous two steps, said recirculating streams having an adjusted pH of between about 7–8; and (e) recovering the purified concentrated Cephamycin C solution, the entire process being conducted at between about 0–5° C.

2. The process of claim 1 in which the pH of step a is about 1.8.

3. The process of claim 1 in which the cation ion exchange resin is a methylene sulfonic acid resin.

4. The process of claim 1 in which the purified concentrated Cephamycin C solution has an end point pH of between 5–6.5.

* * * * *